(12) United States Patent
Park et al.

(10) Patent No.: US 11,516,918 B2
(45) Date of Patent: Nov. 29, 2022

(54) AIR-QUALITY DETECTION APPARATUS

(71) Applicant: LG ELECTRONICS INC., Seoul (KR)

(72) Inventors: Chiwan Park, Seoul (KR); Kijung Sung, Seoul (KR); Hyunho Oh, Seoul (KR); Taedong Shin, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 327 days.

(21) Appl. No.: 16/705,695

(22) Filed: Dec. 6, 2019

(65) Prior Publication Data

US 2020/0187357 A1 Jun. 11, 2020

(51) Int. Cl.
| | | |
|---|---|---|
| *H05K 1/18* | (2006.01) | |
| *G01D 21/02* | (2006.01) | |
| *G01N 33/00* | (2006.01) | |
| *G01N 27/414* | (2006.01) | |
| *G01N 27/12* | (2006.01) | |

(52) U.S. Cl.
CPC ............ *H05K 1/181* (2013.01); *G01D 21/02* (2013.01); *G01N 27/12* (2013.01); *G01N 27/122* (2013.01); *G01N 27/414* (2013.01); *G01N 33/004* (2013.01); *G01N 33/005* (2013.01)

(58) Field of Classification Search
CPC .... G01N 27/12; G01N 27/414; G01N 33/005; G01N 33/004; G01N 27/122; H05K 1/181; G01D 21/02
USPC ...................................................... 73/31.06
See application file for complete search history.

(56) References Cited

U.S. PATENT DOCUMENTS

| | | | |
|---|---|---|---|
| 6,782,351 B2 | 8/2004 | Reichel et al. | |
| 9,993,166 B1 * | 6/2018 | Johnson | A61B 5/0022 |
| 11,030,875 B2 * | 6/2021 | Glynn | G08B 21/14 |
| 11,184,739 B1 * | 11/2021 | Wellig | H04W 4/021 |
| 2003/0051023 A1 * | 3/2003 | Reichel | G01N 33/0075 |
| | | | 709/223 |
| 2009/0308941 A1 * | 12/2009 | Patch | F24F 11/77 |
| | | | 236/49.3 |
| 2017/0241964 A1 * | 8/2017 | Vereecken | G01N 33/0062 |
| 2017/0257967 A1 * | 9/2017 | Obrist | H05K 7/1427 |
| 2019/0154286 A1 * | 5/2019 | Pham | F24F 11/86 |

(Continued)

FOREIGN PATENT DOCUMENTS

| | | | | |
|---|---|---|---|---|
| CH | 710015 A1 * | 2/2016 | | H02G 3/12 |
| CN | 204501797 | * 7/2015 | | A61L 9/20 |

(Continued)

OTHER PUBLICATIONS

Korean Office Action dated Feb. 4, 2020.

(Continued)

*Primary Examiner* — Clayton E. LaBalle
*Assistant Examiner* — Kevin C Butler
(74) *Attorney, Agent, or Firm* — Ked & Associates

(57) ABSTRACT

An air-quality detection apparatus is disclosed. The air-quality detection apparatus includes a casing body including a bottom and a side wall extending upwards from the circumference of the bottom, a first printed circuit board (PCB) disposed horizontally above the bottom, a temperature/humidity sensor mounted on the bottom surface of the first PCB, a second PCB disposed horizontally above the first PCB, and a $CO_2$ sensor mounted on the second PCB.

20 Claims, 15 Drawing Sheets

(56) References Cited

U.S. PATENT DOCUMENTS

| | | | | |
|---|---|---|---|---|
| 2019/0234921 | A1* | 8/2019 | Ahn | G01N 21/85 |
| 2020/0049365 | A1* | 2/2020 | Thoni | F24F 11/89 |
| 2020/0187357 | A1* | 6/2020 | Park | G01N 33/0032 |
| 2020/0261009 | A1* | 8/2020 | Everman | G16H 40/40 |
| 2021/0239335 | A1* | 8/2021 | Morgan | F24F 8/00 |
| 2021/0393834 | A1* | 12/2021 | Wellig | A61L 2/24 |
| 2021/0398230 | A1* | 12/2021 | Gupta | G05B 13/0265 |
| 2022/0001999 | A1* | 1/2022 | Pearce | G01N 33/0063 |

FOREIGN PATENT DOCUMENTS

| | | | | |
|---|---|---|---|---|
| CN | 105823515 | | 8/2016 | |
| CN | 106813315 | | 6/2017 | |
| CN | 108896105 | | 11/2018 | |
| DE | 20-2017-106413 | | 10/2017 | |
| EP | 3070800 | A1 * | 9/2016 | H02G 3/02 |
| EP | 3663754 | A1 * | 6/2020 | G01D 21/02 |
| KR | 10-2003-0010431 | | 2/2003 | |
| KR | 10-2008-0048929 | | 6/2008 | |
| KR | 10-2009-0052167 | | 5/2009 | |
| KR | 10-2009-0067731 | | 6/2009 | |
| KR | 10-2017-0076254 | | 7/2017 | |
| KR | 10-2018-006228 | | 6/2018 | |
| KR | 10-2018-0062628 | | 6/2018 | |
| KR | 10-1912624 | | 10/2018 | |
| WO | WO-2016030082 | A1 * | 3/2016 | H02G 3/12 |
| WO | WO-2018215980 | A1 * | 11/2018 | G05B 15/02 |

OTHER PUBLICATIONS

European Search Report dated May 13, 2020.
Indoor air quality module Ultra fine dust sensor, CO2 sensor, VOC sensor, temperature and humidity sensor, integrated indoor air quality management module; Cubic Dust Sensor Korean Agency FIS Korea Agency; pp. 1-2; blog.daum.net/kurayamida/17.
Korean Notice of Allowance dated Sep. 4, 2020 issued in Application No. 10-2018-0157579.
U.S. Notice of Allowance dated Dec. 22, 2021 issued in U.S. Appl. No. 16/705,762.
U.S. Appl. No. 16/705,762, dated Dec. 6, 2019.
European Search Report dated May 20, 2020 issued in Application No. 19214169.5.

* cited by examiner

AIR-QUALITY DETECTION APPARATUS

CROSS-REFERENCE TO RELATED APPLICATION

This application claims the priority benefit of Korean Patent Application No. 10-2018-0157580, filed on Dec. 7, 2018 in the Korean Intellectual Property Office, the disclosure of which is incorporated herein by reference.

BACKGROUND OF THE INVENTION

1. Field of the Invention

The present disclosure relates to an apparatus for detecting the quality of air.

2. Description of the Related Art

Sensors for detecting the quality of indoor/outdoor air are known. Recently, as it has become generally known that fine dust (PM 10) or ultra-fine dust (PM 2.5) is harmful to the human body, sensors for detecting the quality of indoor/outdoor air have greatly attracted the attention of the general public.

Korean Patent No. 1912624 (hereinafter, referred to as the 'conventional art 1') discloses an outdoor-air-quality detection apparatus that is networked with a user's terminal. The air-quality detection apparatus disclosed in the conventional art 1 is configured to transmit the quality of air detected by a sensor to a network through a communication interface so that a user confirms the quality of air using the user's terminal.

The sensor includes a fine dust sensor, a temperature/humidity sensor, a volatile organic compound detection sensor, and the like, and is configured to detect the overall quality of air.

Although the conventional art 1 suggests that the sensor and the communication interface are mounted on a substrate accommodated in a main body, the concrete structure for mounting these components on the substrate is not described or disclosed.

Since the air-quality detection apparatus of the conventional art 1 is secured to a wall using a fixing frame 40, it is not portable. However, in recent years, since interest in the quality of indoor air in, for example, offices, homes, and the like, as well as the quality of outdoor air is high, a small-sized compact air-quality detection apparatus is required so that a user may easily carry the air-quality detection apparatus and use the same at a desired place.

When an air-quality detection apparatus is configured to detect the overall quality of air using various types of sensors, it is important not only to compactly arrange the sensors to minimize the volume of the apparatus but also to optimize the arrangement of the sensors so that each sensor does not affect the accuracy of detection by other sensors.

In particular, in order to accurately detect values (temperature and humidity) using a temperature/humidity sensor, it is preferable to avoid disposing a heat-generating element near the temperature/humidity sensor. However, some types of sensors inevitably generate a large amount of heat during operation. For example, a dust sensor includes a heater for heating air. Thus, when the dust sensor and the temperature/humidity sensor are disposed in a compact structure and accommodated in a single casing, there is the need to devise a structure for preventing the heat generated by the dust sensor from affecting the accuracy of detection by the temperature/humidity sensor.

SUMMARY OF THE INVENTION

Therefore, the present disclosure has been made in view of the above problems, and the first object of the present disclosure is to provide an air-quality detection apparatus in which, when a temperature/humidity sensor and another sensor, which is a heat-generating element, are accommodated in a single casing, the influence of heat generated by the other sensor on the temperature/humidity sensor is reduced.

The second object of the present disclosure is to provide an air-quality detection apparatus in which a heat insulation structure is formed in a casing in order to prevent heat generated by a dust sensor from being transferred to a temperature/humidity sensor, and the heat insulation structure is realized using a printed circuit board (PCB) having the temperature/humidity sensor mounted thereon without using a separate heat insulation material or heat blocking material.

The third object of the present disclosure is to provide an air-quality detection apparatus in which a separate vent hole for detecting temperature and humidity is not formed in a casing, but a hole for guiding air to a dust sensor or a coupling member passage hole necessary for the assembly of a cover is used as a passage for guiding external air to a temperature/humidity sensor.

The fourth object of the present disclosure is to provide an air-quality detection apparatus that is compact by optimizing the arrangement of sensors and PCBs accommodated in a casing, particularly, by realizing compact arrangement of the sensors while securing the accuracy of the respective sensors.

The fifth object of the present disclosure is to provide an air-quality detection apparatus in which PCBs on which sensors are mounted are disposed in a multi-layered structure in a casing, thereby enabling convenient assembly and maintenance/repair of the PCBs.

The sixth object of the present disclosure is to provide an air-quality detection apparatus having an Internet-of-Things (IoT) function capable of transmitting the detected air quality over a communication network.

In accordance with an aspect of the present disclosure, the above and other objects can be accomplished by the provision of an air-quality detection apparatus including a first printed circuit board (PCB) and a second PCB mounted in a casing body. The casing body may include a bottom and a side wall extending upwards from the circumference of the bottom, the first PCB may be disposed horizontally above the bottom, and the second PCB may be disposed horizontally above the first PCB.

A temperature/humidity sensor may be mounted on the bottom surface of the first PCB. A CO2 sensor may be mounted on the second PCB. Since the temperature/humidity sensor and the CO2 sensor are disposed at opposite positions, with the first PCB interposed therebetween, the first PCB may prevent heat generated by the CO2 sensor from being transferred to the temperature/humidity sensor.

When the first PCB is viewed from above, the temperature/humidity sensor may be disposed in a region that does not overlap the CO2 sensor. The CO2 sensor may be mounted on the bottom surface of the second PCB.

The casing body may include a support rib protruding from the bottom to support the bottom surface of the first PCB. The temperature/humidity sensor may be disposed within an interval by which the first PCB is spaced apart from the bottom by the support rib.

A gap may be formed between the first PCB and the side wall such that a space between the bottom and the bottom surface of the first PCB, spaced apart from the bottom by the support rib, communicates with the space above the first PCB therethrough.

A dust sensor may be disposed above the first PCB. The first PCB may prevent heat generated by the dust sensor from being transferred to the temperature/humidity sensor.

A third PCB may be disposed horizontally above the second PCB, and the dust sensor may be mounted on the top surface of the third PCB. The dust sensor may include a chamber mounted on the top surface of the third PCB to receive air introduced thereinto and a light emitter configured to emit light into the chamber. The chamber may include at least one communication hole formed therein to allow external air to flow into and out of the chamber.

A cover may be provided to cover an open top surface defined opposite the bottom by the side wall. The cover may include at least one vent hole formed therein so as to overlap the at least one communication hole when viewed from above. A portion of the at least one vent hole that does not overlap the at least one communication hole may communicate with the gap through the space in the casing body.

The air-quality detection apparatus may further include an exterior panel including a lid disposed above the cover and a locking hook protruding downwards from the lid to be coupled to the casing body. The cover may include a hook passage formed therein to allow the locking hook to pass therethrough. A gap may be formed between the locking hook and the hook passage so as to communicate with the interior of the casing body.

BRIEF DESCRIPTION OF THE DRAWINGS

The above and other objects, features and other advantages of the present disclosure will be more clearly understood from the following detailed description taken in conjunction with the accompanying drawings, in which.

DETAILED DESCRIPTION OF THE PREFERRED EMBODIMENTS

Figure 1:
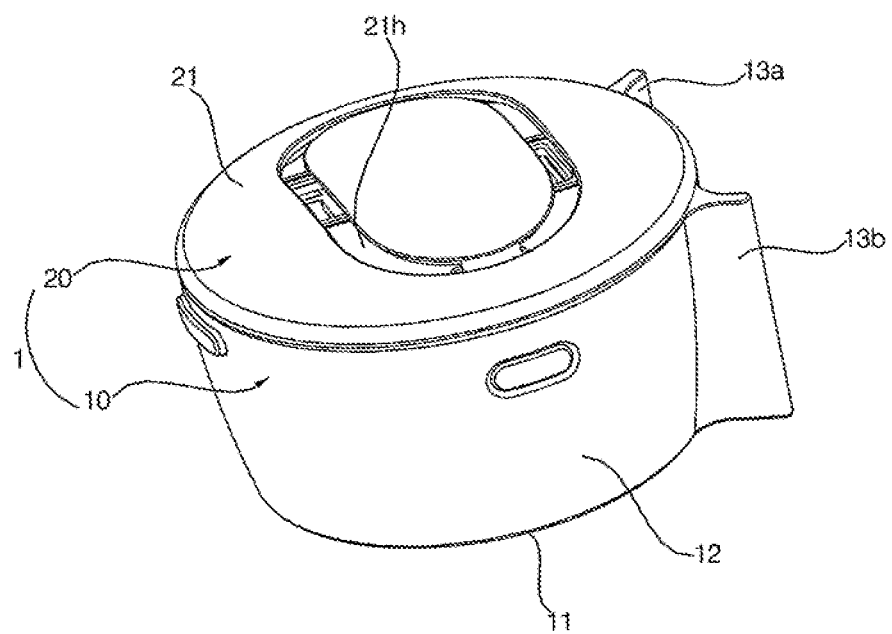
FIG. 1 is a perspective view of an air-quality detection apparatus according to an embodiment of the present disclosure.

Advantages and features of the present disclosure and methods for achieving them will be made clear from the embodiments described below in detail with reference to the accompanying drawings. The present disclosure may, however, be embodied in many different forms, and should not be construed as being limited to the embodiments set forth herein. Rather, these embodiments are provided so that this disclosure will be thorough and complete, and will fully convey the scope of the present disclosure to those skilled in the art. The present disclosure is merely defined by the scope of the claims. Like reference numerals refer to like elements throughout the specification.

Figure 2:
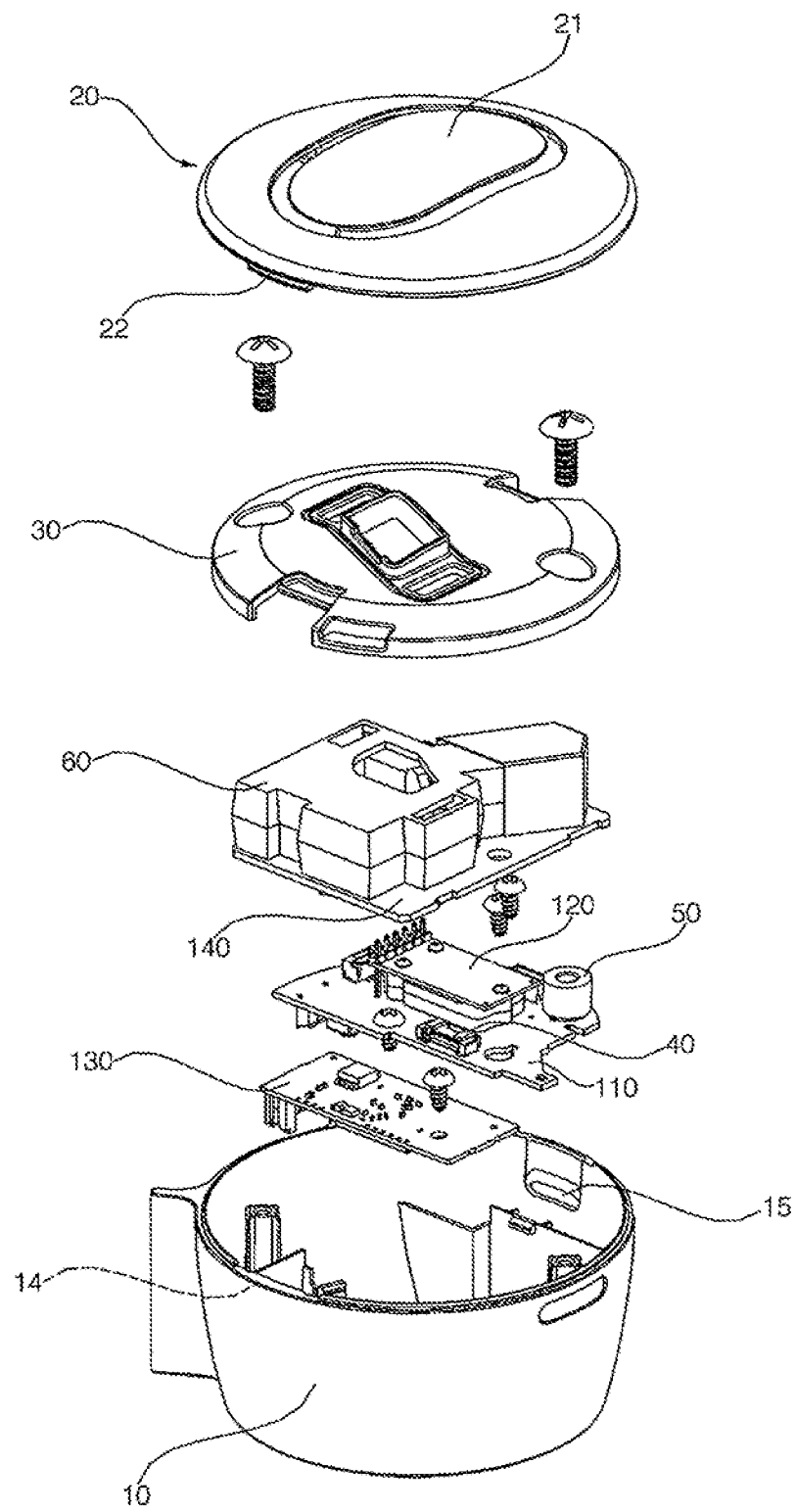
FIG. 2 is an exploded perspective view of the air-quality detection apparatus shown in FIG. 1.

FIG. 1 is a perspective view of an air-quality detection apparatus according to an embodiment of the present disclosure. FIG. 2 is an exploded perspective view of the air-quality detection apparatus shown in FIG. 1. Referring to FIGS. 1 and 2, an air-quality detection apparatus according to an embodiment of the present disclosure includes a casing 1 forming the external appearance of the air-quality detection apparatus, two or more printed circuit boards (PCBs) 110, 120, 130 and 140 disposed in the casing 1, and two or more sensors mounted on the PCBs 110, 120, 130 and 140.

The casing 1 may include a casing body 10, having an open top surface and defining a predetermined accommodation space therein, and an exterior panel 20 covering the open top surface of the casing body 10. The casing body 10 may include a bottom 11 and a side wall 12. The bottom 11 may be formed in a substantially circular and flat shape, and the side wall 12 may be formed in a cylindrical shape extending upwards from the circumference of the bottom 11. The side wall 12 may have a truncated cone shape in which the inner and outer diameters of the cross-section thereof gradually increase toward the upper side thereof (or from the bottom 11 of the casing body 10 to the top surface of the casing body 10).

The casing body 10 may include a pair of stands 13a and 13b protruding from the outer surface of the side wall 12. The pair of stands 13a and 13b may be spaced apart from each other in a circumferential direction, and may protrude from the side wall 12 in a radial direction. The air-quality detection apparatus may stand upright due to the pair of stands 13a and 13b such that the exterior panel 20 is oriented forwards.

The exterior panel 20 may include a lid 21 having a vent hole 21h formed therein, and may further include a hinge lock 22 and a locking hook 23, which protrude from the rear surface of the lid 21. The hinge lock 22 and the locking hook 23 may be disposed at opposite sides of the lid 21 so as to be symmetrical to each other with respect to the center of the lid 21. The vent hole 21h may be formed along a substantially annular-shaped path. However, the vent hole 21h may not be formed in some regions of the path, such that an inner portion of the lid 21, which is surrounded by the path, is connected to an outer portion of the lid 21.

The casing body 10 may have a latching recess 14 formed in the circumference of the open upper end thereof such that the hinge lock 22 is caught therein. In addition, the casing body 10 may have a locking recess 15 formed in the inner surface of the side wall 12 such that the locking hook 23 is caught therein. In order to assemble the exterior panel 20 to the casing body 10, the hinge lock 22 is first fitted into the latching recess 14 by tilting the exterior panel 20 with respect to the casing body 10, and then the locking hook 23 is fitted into the locking recess 15 by rotating the exterior panel 20 about the latching recess 14 such that the locking hook 23 is moved downwards.

A cover 30 covering the casing body 10 may be further provided. The cover 30 is disposed between the casing body 10 and the exterior panel 20 to cover the open top surface of the casing body 10. The cover 30 may have at least one vent hole 31, 32 and 33 formed therein to allow external air to enter the casing body 10. The vent hole 31, 32 and 33 may include a first vent hole 31 formed in the center of the cover 30, and second and third vent holes 32 and 33 formed in regions of the cover 30 on opposite sides of the first vent hole 31.

The cover 30 may have a hinge lock passage 34 and a hook passage 35 formed in regions thereof that respectively correspond to the position of the hinge lock 22 and the position of the locking hook 23, which are formed at the exterior panel 20.

Figure 3:
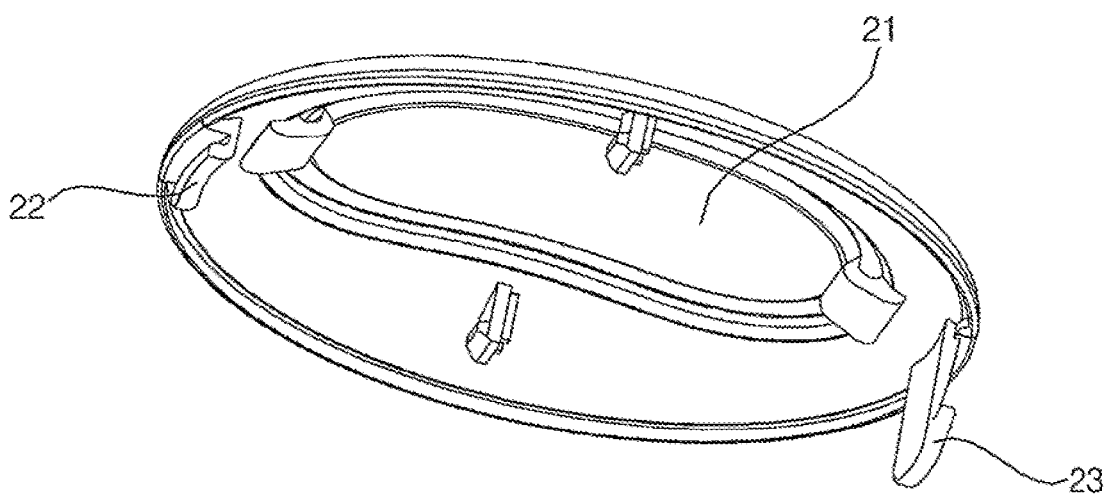
FIG. 3 is a perspective view of the exterior panel shown in FIG. 1.
Figure 4:
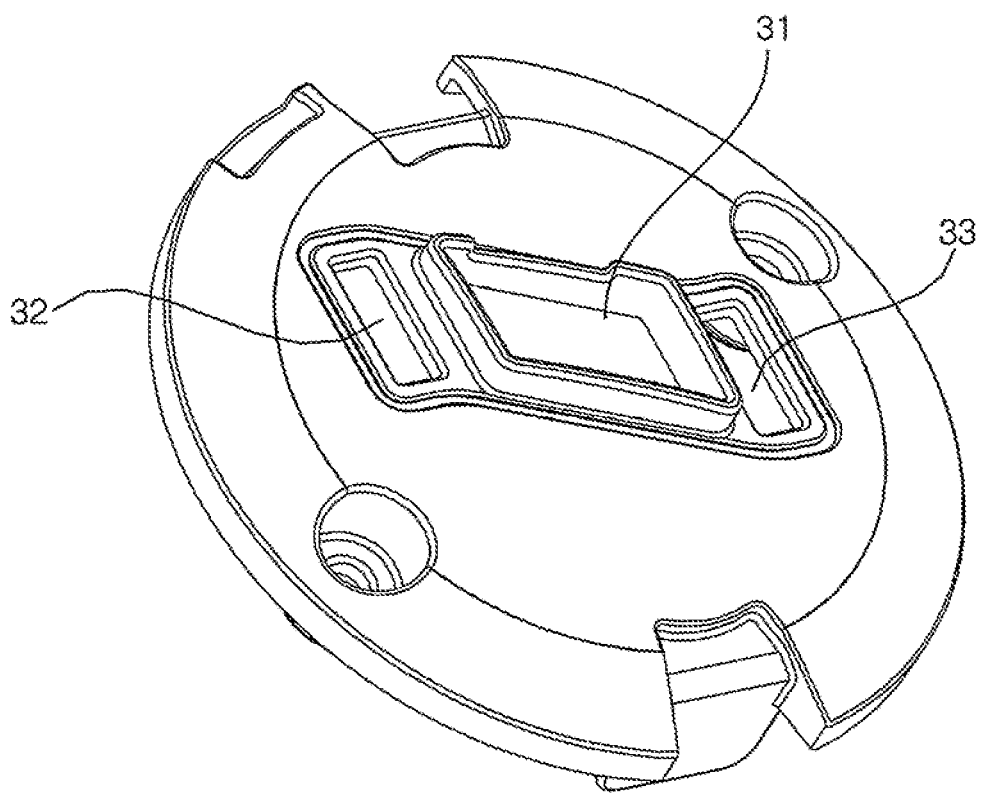
FIG. 4 is a perspective view of the cover shown in FIG. 2.
Figure 5:
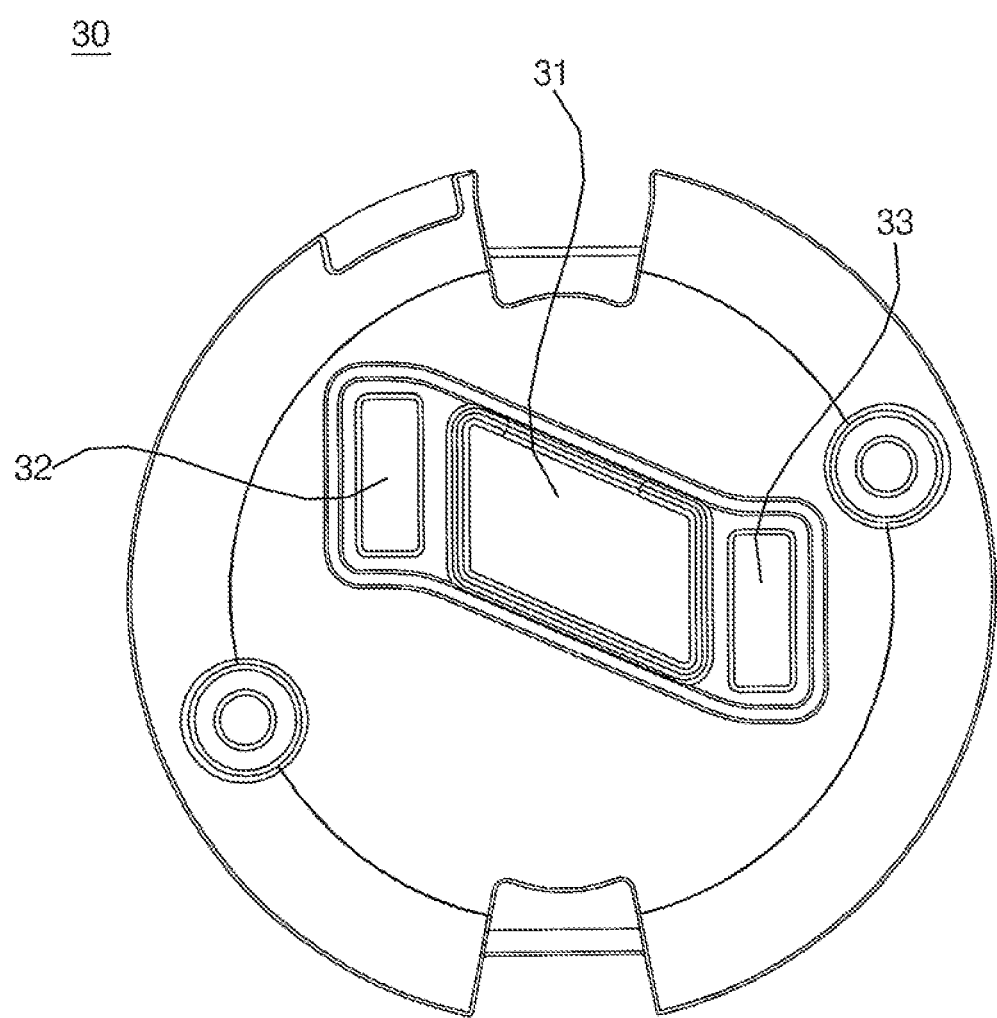
FIG. 5 is a plan view of the cover shown in FIG. 4.
Figure 6:
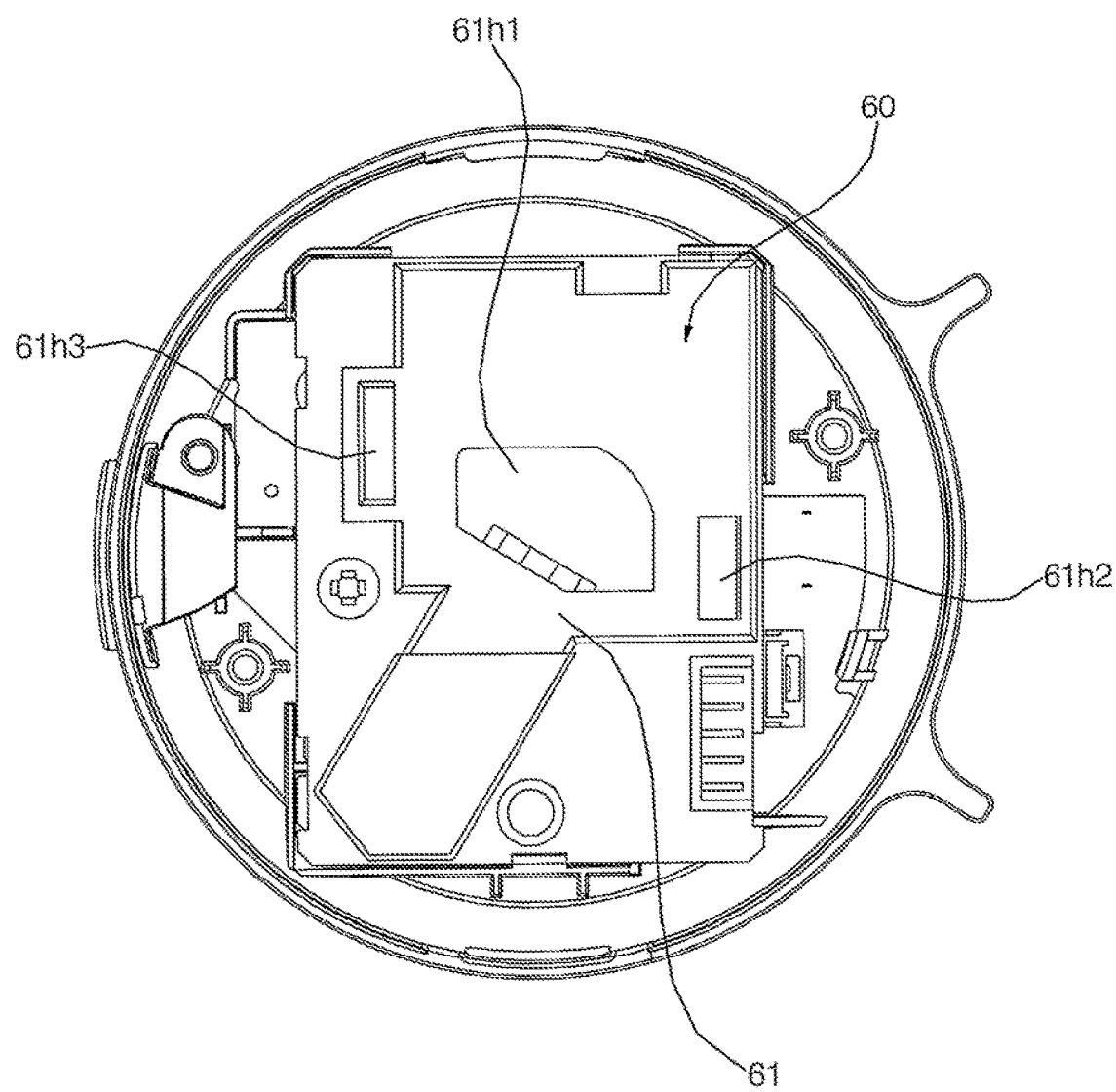
FIG. 6 is a partially exploded view of the air-quality detection apparatus shown in FIG. 1.
Figure 7:
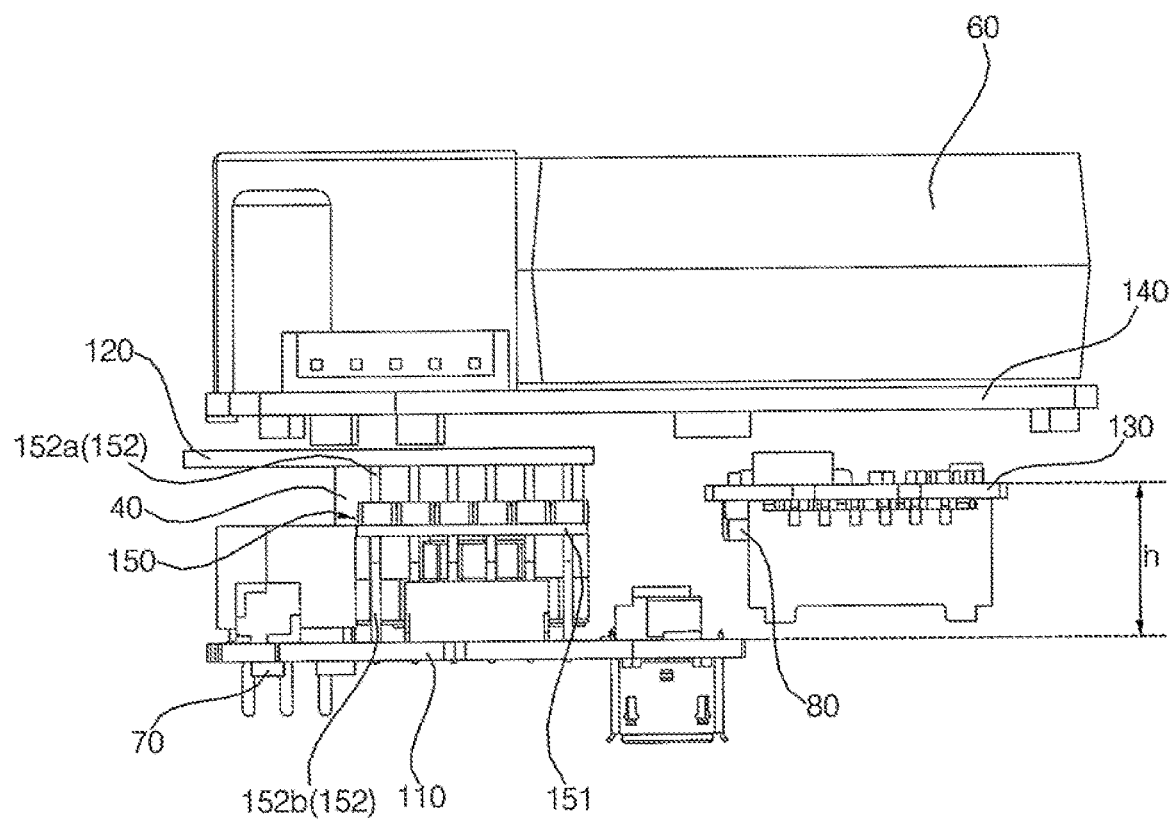
FIG. 7 is a side view of FIG. 6, with a casing body removed.
Figure 8:
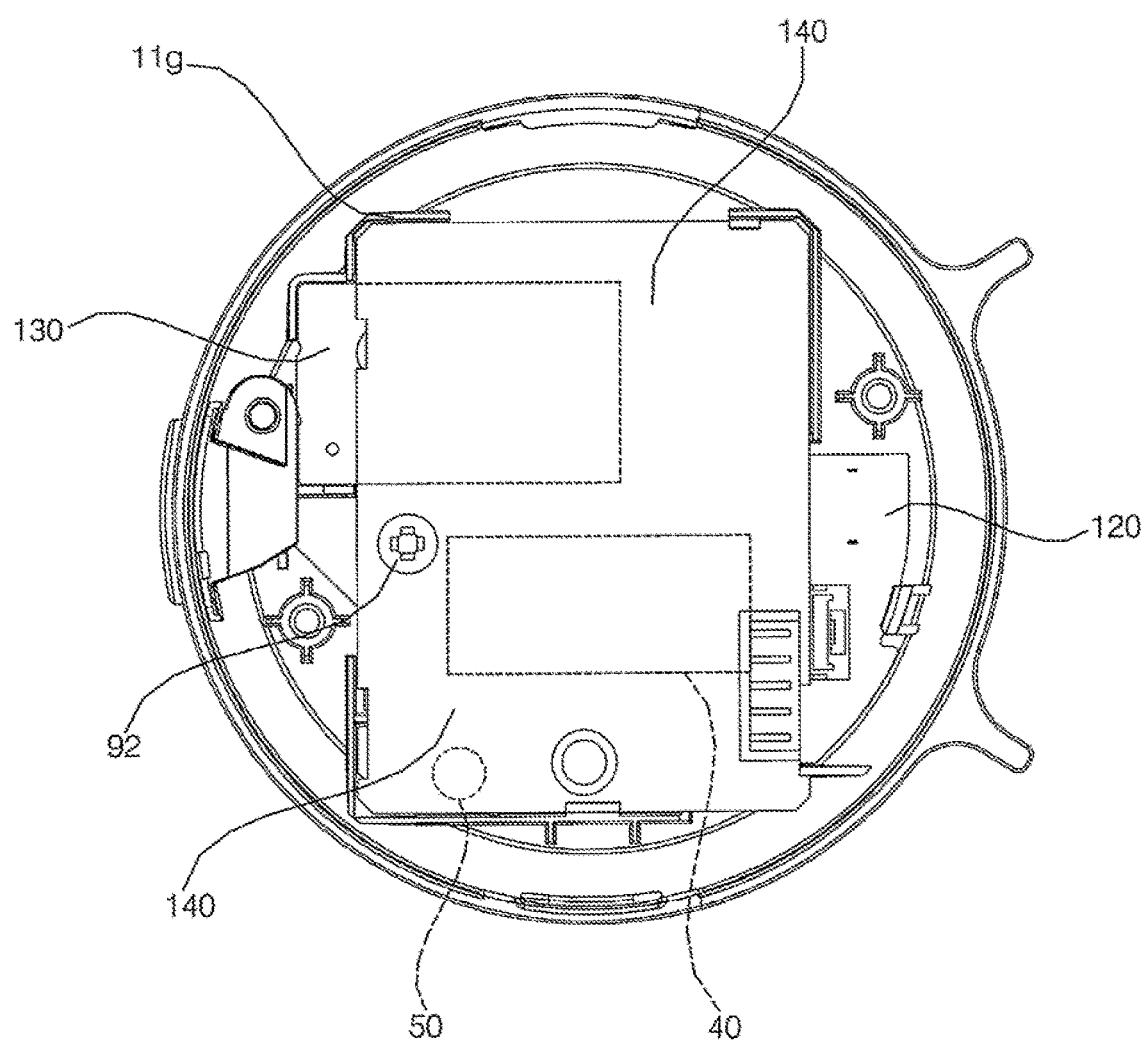
FIG. 8 is a view of the assembly shown in FIG. 6, with a dust sensor removed.
Figure 9:
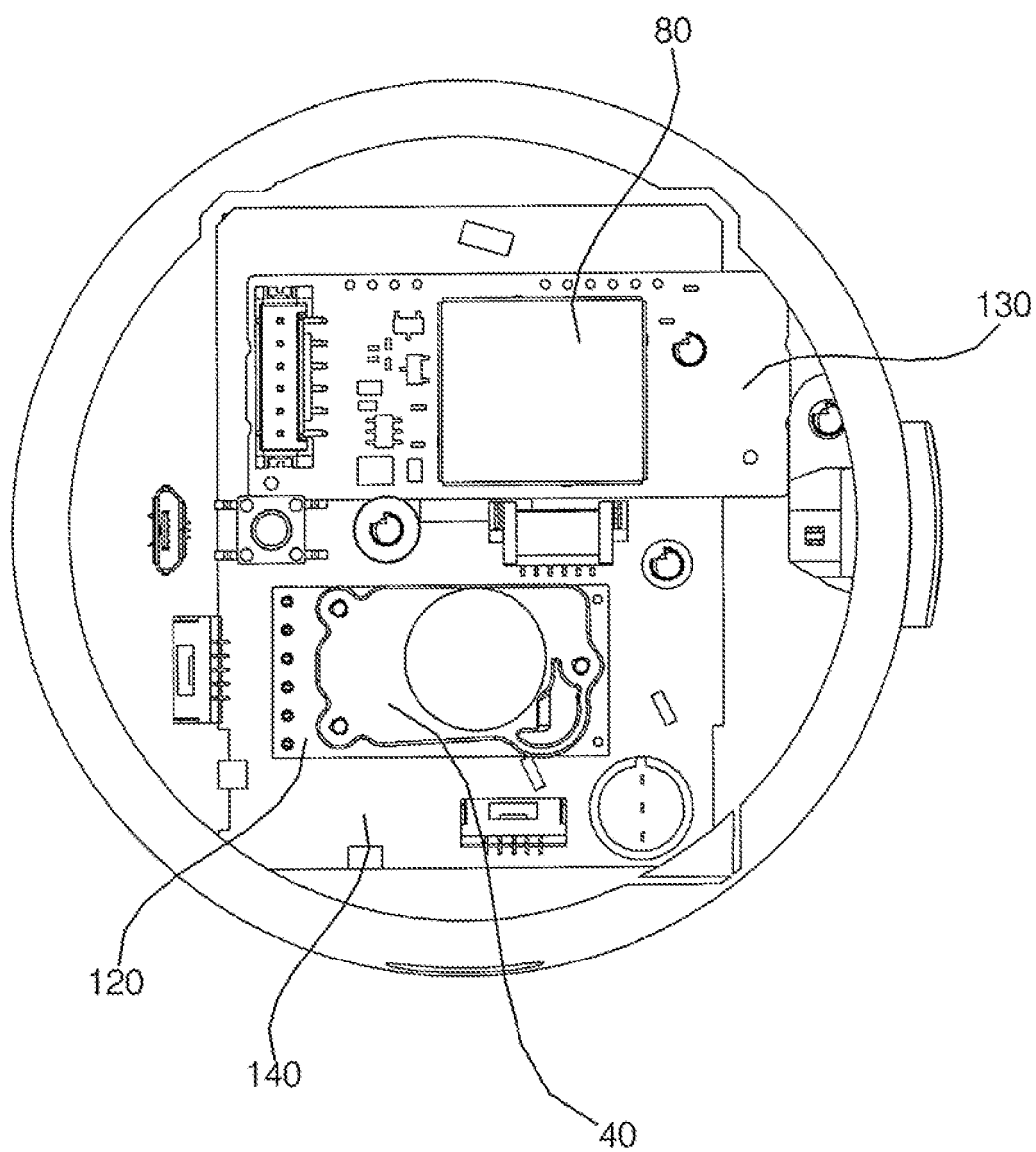
FIG. 9 is a bottom view of a third printed circuit board (PCB)
Figure 10:
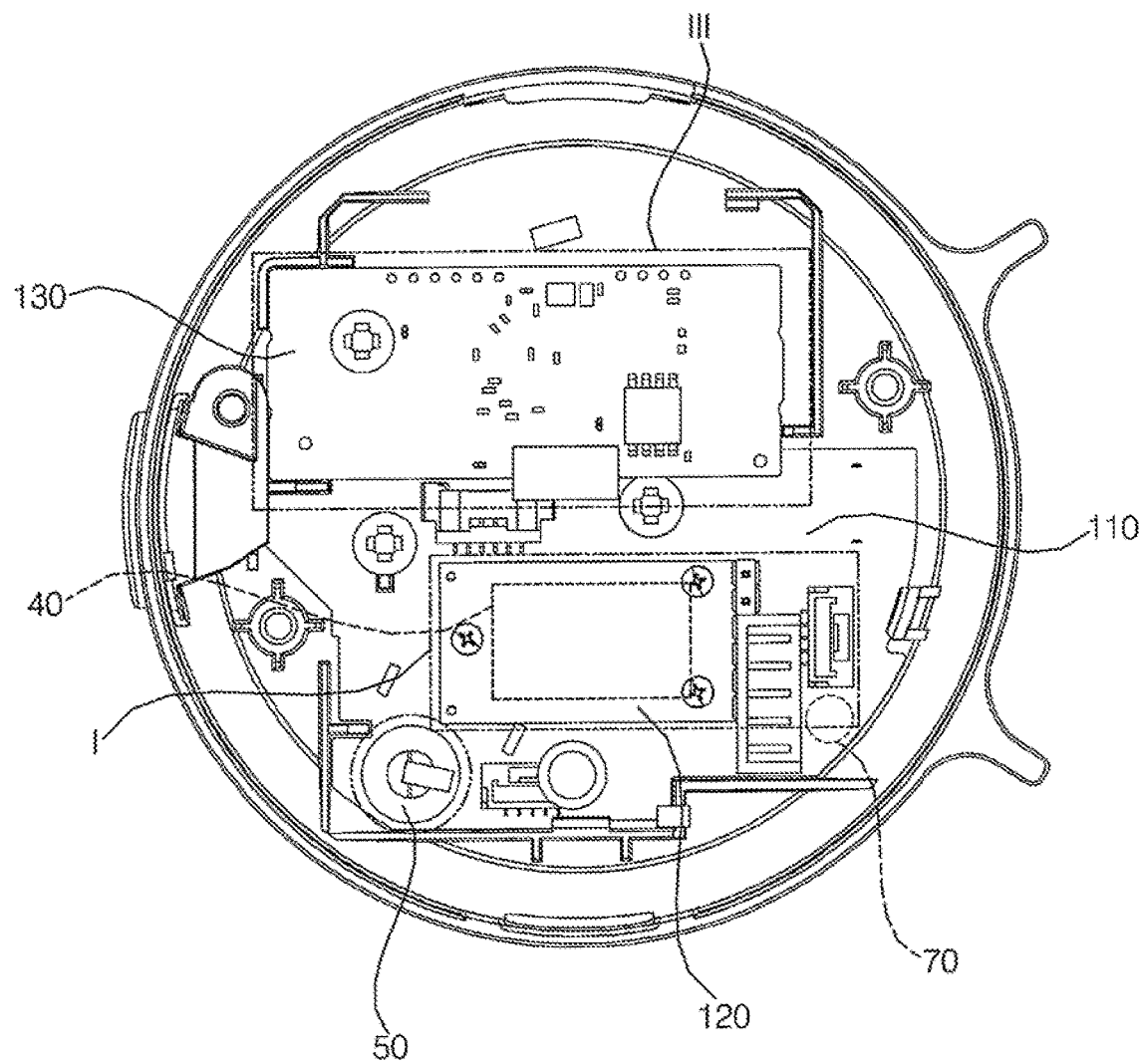
FIG. 10 is a view of the assembly shown in FIG. 8, with the third PCB removed.
Figure 11:
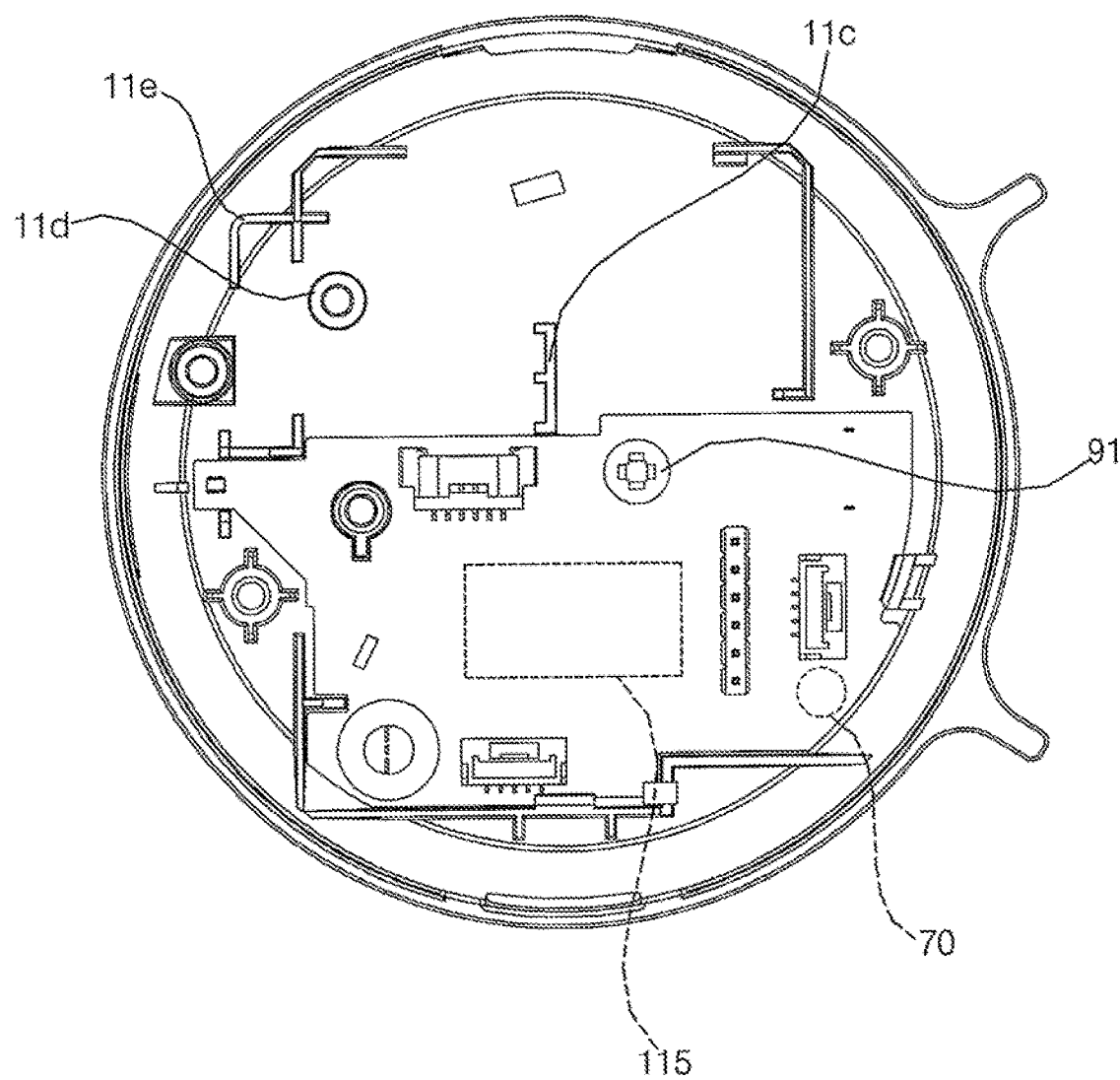
FIG. 11 is a view of the assembly shown in FIG. 10, with a second PCB and a fourth PCB removed.
Figure 12:
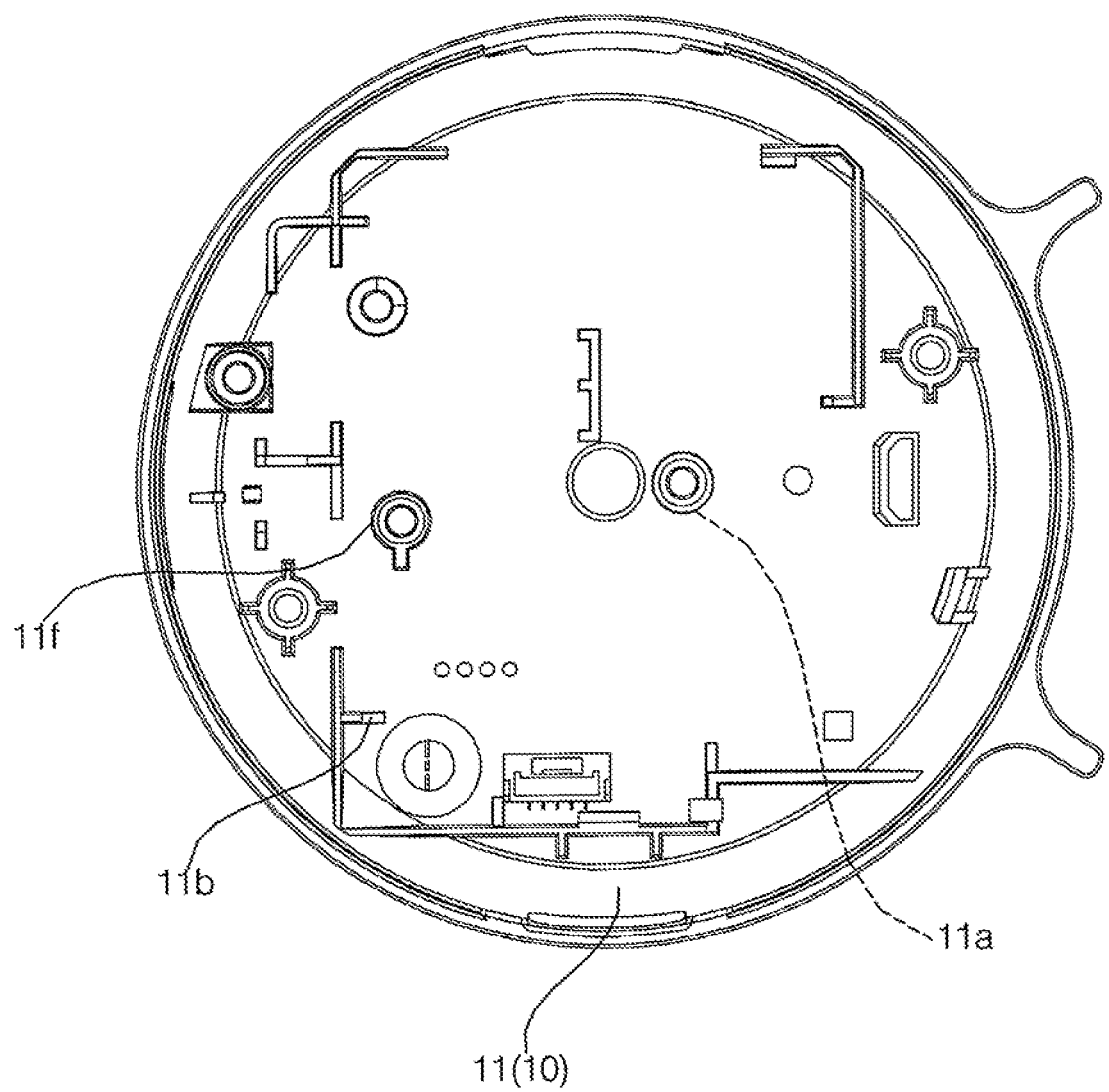
FIGS. 12 and 13 are views of the casing body.
Figure 13:
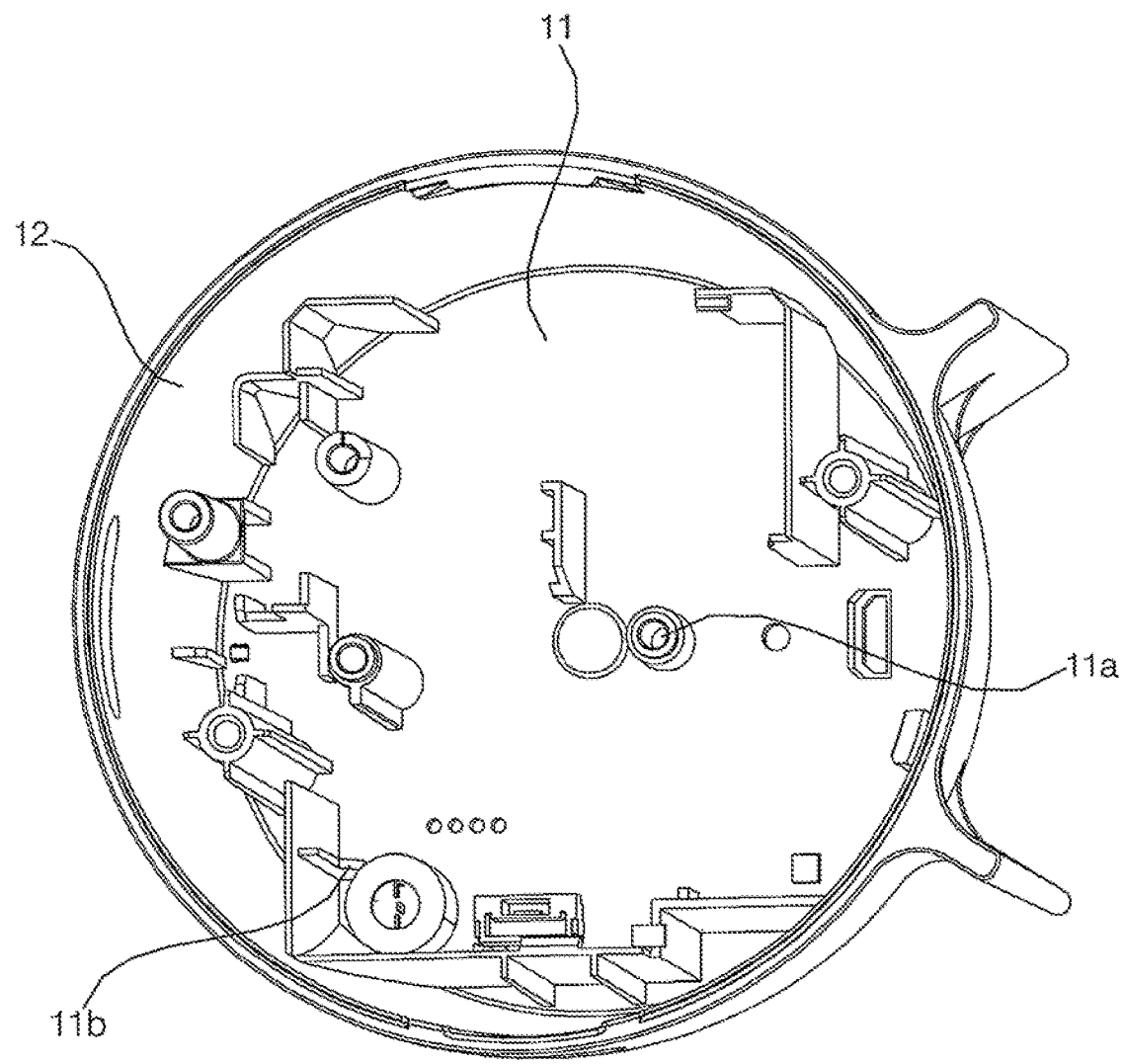
Figure 14:
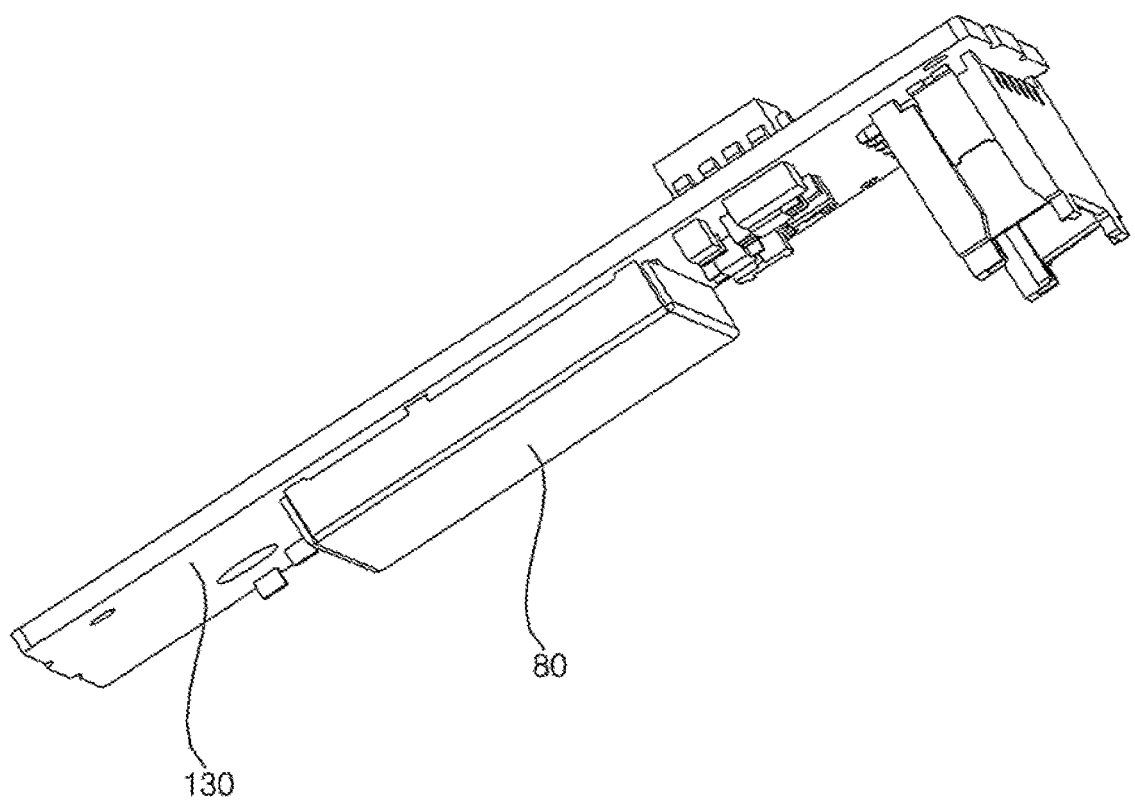
FIG. 14 is a view of the fourth PCB, on which a wireless communication interface is mounted.
Figure 15:
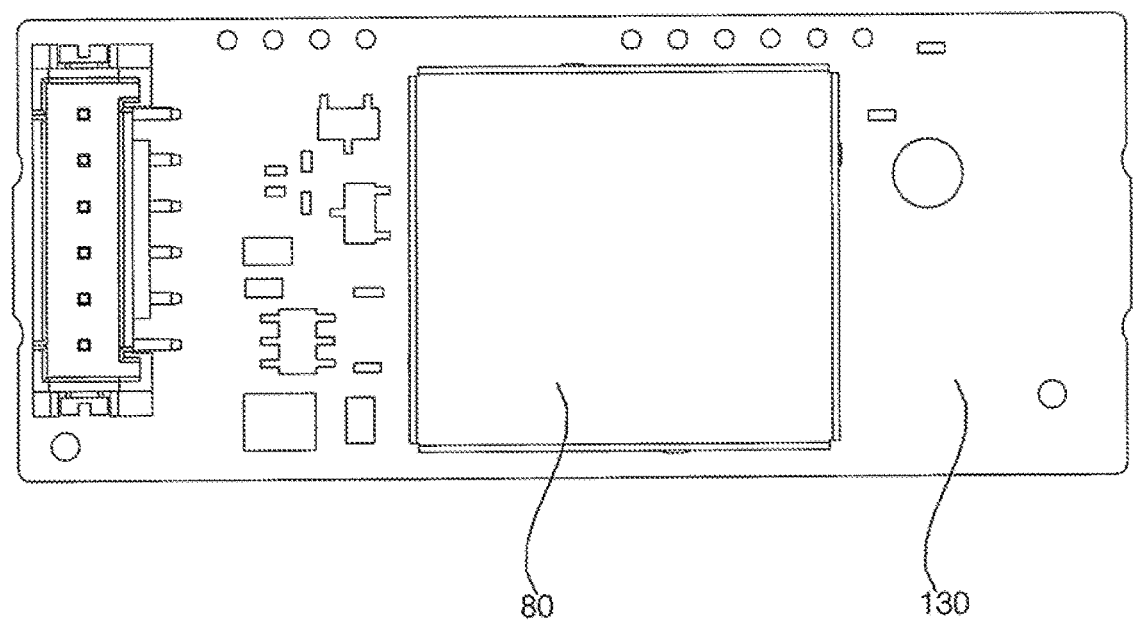
FIG. 15 is a bottom view of FIG. 14.

FIG. 3 is a perspective view of the exterior panel shown in FIG. 1. FIG. 4 is a perspective view of the cover shown in FIG. 3 FIG. 5 is a plan view of the cover shown in FIG. 4. FIG. 6 is a partially exploded view of the air-quality detection apparatus shown in FIG. 1. FIG. 7 is a side view of FIG. 6, with the casing body removed. FIG. 8 is a view of the assembly shown in FIG. 6, with a dust sensor removed. FIG. 9 is a bottom view of a third PCB. FIG. 10 is a view of the assembly shown in FIG. 8, with the third PCB removed. FIG. 11 is a view of the assembly shown in FIG. 10, with a second PCB and a fourth PCB removed. FIGS. 12 and 13 are views of the casing body. FIG. 14 is a view of the fourth PCB, on which a wireless communication interface is mounted. FIG. 15 is a bottom view of FIG. 14.

Referring to FIGS. 1 to 15, a first PCB 110 may be disposed in the casing body 10. The first PCB 110 may be disposed substantially horizontally (or parallel to the bottom 11) above the bottom 11. A processor 115 may be mounted on the bottom surface of the first PCB 110.

The processor 115 may process the values detected by a CO2 sensor 40, a volatile organic compound (VOC) sensor 50, a dust sensor 60, and/or a temperature/humidity sensor 70, and may transmit the processed values through a wireless communication interface 80. This data may be transmitted to a user's terminal through a communication network.

The first PCB 110 may be spaced apart from the bottom 11 of the casing body 10. At least one support rib 11b, which protrudes upwards from the bottom 11, is in contact with the bottom surface of the first PCB 110. Thereby, the position of the first PCB 110 may be maintained at a predetermined height apart from the bottom 11.

A support post 11a may protrude from the bottom 11. The support post 11a may have a cylindrical shape, and may be formed such that a screw is fastened thereinto through an open upper end thereof. The first PCB 110 may be supported by the support post 11a, and may have a screw hole formed therein to communicate with the hollow portion in the support post 11a. A screw 91 may pass through the screw hole from above and may be fastened into the hollow portion.

The height to which the support rib 11b and/or the support post 11a protrude from the bottom 11 may be set to a value that allows the processor 115 to be spaced apart from the bottom 11. Preferably, the height may be set to a value that allows the temperature/humidity sensor 70 mounted on the bottom surface of the first PCB 110 to be spaced apart from the bottom 11, which will be described later. Thus, when a first height to which the temperature/humidity sensor 70 protrudes from the bottom surface of the first PCB 110 (or the distance from the bottom surface of the first PCB 110 to the lower end of the temperature/humidity sensor 70) is greater than a second height to which the processor 115 protrudes from the bottom surface of the first PCB 110 (or the distance from the bottom surface of the first PCB 110 to the lower end of the processor 115), any one of the support rib 11b and the support post 11a needs to protrude further upwards from the bottom 11 than the first height.

Various types of sensors for detecting the quality of air may be accommodated in the casing body 10. Among the sensors accommodated in the casing body 10, the VOC sensor 50 is used to detect volatile organic compounds contained in the air. The VOC sensor 50 may include a heater embedded in a ceramic tube. The heater may be configured to use heat generated by a platinum heating wire through which current flows. The resistance of the circuit is increased and the current is decreased by the combustion reaction of the air around the heater. When gas composed of volatile organic compounds, such as formaldehyde, toluene, benzene, xylene, and an organic solvent, is contained in the air, the resistance of the circuit is decreased, and thus current flows smoothly. Therefore, the processor 115 may detect volatile organic compounds contained in the air based on the output (current or voltage) from the VOC sensor 50.

The VOC sensor 50 may be mounted on the top surface of the first PCB, particularly, in a second region that is closer to the side wall 12 than a first region occupied by the CO2 sensor 40. That is, when viewed from above, the VOC sensor 50 is disposed closer to the side wall 12 than the CO2 sensor 40. The space between the CO2 sensor 40 and the side wall 12 is utilized for the placement of the VOC sensor 50. In particular, since the VOC sensor 50 is smaller than the CO2 sensor 40, the VOC sensor 50 is mounted on the first PCB 110 without using a separate PCB. The VOC sensor 50 is disposed in the second region, which does not interfere with the first region occupied by the CO2 sensor 40, which is connected to the first PCB 110 via a header pin 150, thereby improving space utilization. The VOC sensor 50 may reach a position higher than the height at which a second PCB 120 to be described later is located.

The CO2 sensor 40 for detecting carbon dioxide (CO2) contained in the air may be accommodated in the casing body 10. The CO2 sensor 40 may be an infrared gas sensor (or a nondispersive infrared (NDIR) sensor). The NDIR sensing method is a method of calculating the concentration of a specific ingredient on the basis of the principle that gaseous substances such as CO or CO2 have a specific absorption spectrum with respect to infrared light. The CO2 sensor 40 using the NDIR sensing method may include a light emitter (not shown) for emitting infrared light of a specific frequency band that is absorbed by carbon dioxide, and a light receiver (not shown) for receiving infrared light that is not absorbed by carbon dioxide molecules.

The second PCB 120 is disposed horizontally in a predetermined first region above the first PCB 110. The CO2 sensor 40 is mounted on the second PCB 120. The header pin 150 may be provided to electrically connect the first PCB 110 to the second PCB 120. The second PCB 120 may be spaced apart from the first PCB 110 by the header pin 150.

The header pin 150 may include a pin holder 151 located on the bottom surface of the first PCB 110 and a plurality of pin terminals 152 penetrating the pin holder 151 in a vertical direction. Upper portions 152a of the pin terminals 152, which extend above the pin holder 151, may penetrate the second PCB 120 and may be soldered to the top surface of the second PCB 120, and lower portions 152*b* of the pin terminals 152, which extend below the pin holder 151, may penetrate the first PCB 110 and may be soldered to the bottom surface of the first PCB 110.

The $CO_2$ sensor 40 is preferably disposed on the bottom surface of the second PCB 120. The $CO_2$ sensor 40 is disposed such that the light emitter and the light receiver are oriented downwards. The length of the lower portion 152*b* of each of the pin terminals 152 needs to be set to a value that allows at least the $CO_2$ sensor 40 to be spaced apart from the first PCB 110. The $CO_2$ sensor 40 may detect the quality of air present within the interval between the $CO_2$ sensor 40 and the first PCB 110. Preferably, the $CO_2$ sensor 40 is spaced 2.8 mm or more apart from the first PCB 110.

The wireless communication interface 80 may be accommodated in the casing body 10. The wireless communication interface 80 is wirelessly connected to a communication network to transmit and receive data signals. The wireless communication interface 80 may communicate with a gateway, an access point, and/or a hub, which constitute the communication network, according to a preset communication protocol. The communication may be performed based on wireless communication technology such as Wi-Fi, ZigBee, Z-wave, or Bluetooth.

Wi-Fi was originally the brand name of Wi-Fi Alliance, but now it is commonly used to refer to wireless communication technology. Wi-Fi refers to a series of technologies that support WLAN connection between devices, WLAN connection between device connections (Wi-Fi P2P), and PAN/LAN/WAN configuration according to standards defined in IEEE 802.11. Hereinafter, the term "Wi-Fi module" indicates a wireless communication interface 80 that performs wireless communication based on Wi-Fi technology.

ZigBee is wireless network technology for performing communication by configuring a private communication network using a small-sized low-power digital radio. ZigBee is communication technology defined in IEEE 802.15. ZigBee devices are small and inexpensive and consume a relatively small amount of power, and thus are drawing attention as a solution for establishing the ubiquitous Internet, such as a home network, and are used in short-range communication for home and building networks and in industrial facility automation, logistics, human interfaces, telematics, environment monitoring, military, etc.

The ZigBee protocol is composed of a physical layer, a media access control (MAC) layer, a network layer, and an application layer. The physical layer and the MAC layer of ZigBee are defined in the IEEE 802.15.4 standard.

The ZigBee network layer supports routing and addressing for a tree structure and a mesh structure, and ZigBee Home Automation Public Profile and ZigBee Smart Energy Profile are typically used as an application profile. In addition, the new ZigBee specification RF4CE defines a simple network stack for solution of home appliance remote control and start topology. RF4CE uses a 2.4 GHz frequency band and provides encryption using AES-128.

ZigBee is generally used in fields in which a long battery life and encryption are required despite a low transmission speed, and is appropriate for periodic or intermittent data transmission or for data transmission for simple signal transmission of a sensor and an input device. ZigBee is applied to a wireless lighting switch, a home electronic power system, a traffic management system, and any other private or industrial device that requires short-range low-speed communication. ZigBee is more simple and inexpensive than other WPAN technologies such as Bluetooth or Hereinafter, the term "ZigBee module" indicates a wireless communication interface 80 that performs wireless communication based on ZigBee technology.

Z-wave is wireless transmission technology designed for a device that requires low power and a low bandwidth, such as home automation and sensor networks. Z-wave primarily aims to provide reliable communication between one or more nodes and a controller on a wireless network. Z-wave is composed of a physical layer, a MAC layer, a transmission layer, a routing layer, and an application layer. Z-wave uses a frequency band around 900 MHz (e.g. 869 MHz in Europe and 908 MHz in the United States) and a frequency band around 2.4 GHz, and provides speeds of 9.6 kbps, 40 kbps and 200 kbps. Hereinafter, the term "Z-wave module" indicates a wireless communication interface 80 that performs wireless communication based on Z-wave technology.

The fourth PCB 130 is disposed horizontally at a position spaced further upwards apart from the bottom 11 of the casing body 10 than the first PCB 110. The wireless communication interface 80 is mounted on the fourth PCB 130. The wireless communication interface 80 is preferably mounted on the bottom surface of the fourth PCB 130. However, in some embodiments, the wireless communication interface 80 may be mounted on the top surface of the fourth PCB 130.

When the bottom 11 is viewed from above, at least a portion of the fourth PCB 130 is disposed in a third region that does not overlap the first PCB 110. That is, when the bottom 11 is viewed from above, the first PCB 110 and the fourth PCB 130 may be disposed in respective regions into which the bottom 11 is substantially bisected, but may partially overlap each other.

In particular, a support rib 11*c* and a mount boss 11*d* may protrude from the bottom 11 below the fourth PCB 130. The support rib 11*c* may protrude up to a height at which the support rib 11*c* contacts the bottom surface of the fourth PCB 130 and/or the wireless communication interface 80. In addition, a retaining rib 11*e* may protrude from the bottom 11 so as to surround the circumference of the fourth PCB 130. The fourth PCB 130 may have a first side (e.g. a horizontal side) and a second side (e.g. a vertical side) that intersects the first side. The fourth PCB 130 may have a substantially rectangular shape. The retaining rib 11*e* may be formed in an "L" shape that surrounds the first side and the second side to restrain horizontal movement (shaking) of the fourth PCB 130.

The dust sensor 60 for detecting dust contained in the air may be accommodated in the casing body 10. The dust sensor 60 may include a heater (e.g. a circuit resistance), a light emitter (e.g. an infrared LED), a light receiver (e.g. a photodiode detector) for detecting light emitted from the light emitter, and a chamber 61, which accommodates the above components and has an air suction hole 61*h*1 and air discharge holes 61*h*2 and 61*h*3 formed therein.

Dust introduced into the chamber through the air suction hole moves upwards along with an ascending air current generated by the heater. The light (e.g. infrared light) emitted from the light emitter is scattered by the dust. The light receiver detects the scattered light and outputs a pulse waveform corresponding thereto. A portion of the chamber that surrounds the photodiode detector may be surrounded by an electromagnetic shielding member (e.g. a metal plate). The processor 115 may detect dust in the air based on the output (e.g. a pulse waveform) from the light receiver.

The third PCB 140 may be horizontally disposed above the second PCB 120 and the fourth PCB 130 inside the casing body 10. The dust sensor 60 is mounted on the top surface of the third PCB 140. When the bottom 11 is viewed from above, at least a portion of the fourth PCB 130 may overlap the third PCB 140.

In addition, when the bottom 11 is viewed from above, the third PCB 140 may overlap the CO2 sensor 40 and the VOC sensor 50. The dust sensor 60 is larger than the CO2 sensor 40, and therefore, the third PCB 140, on which the dust sensor 60 is mounted, is also larger than the second PCB 120, on which the CO2 sensor 40 is mounted. Thus, in the case in which the third PCB 140 is disposed in the same layer as the second PCB 120, the horizontal area of the air-quality detection apparatus increases. For this reason, the third PCB 140 is disposed above the second PCB 120 and the fourth PCB 130. In this case, when viewed from above, the third PCB 140 may completely cover the second PCB 120, and may also cover the VOC sensor 50.

The chamber 61 of the dust sensor 60 is located above the third PCB 140. Thus, the light emitter and the light receiver, which are accommodated in the chamber 61, as well as the air suction hole 61$h$1 and the air discharge holes 61$h$2 and 61$h$3, which are formed in the chamber 61, are located above the third PCB 140.

As described above, the CO2 sensor 40 is mounted on the second PCB 120 located below the third PCB 140. In particular, the CO2 sensor 40 is mounted on the bottom surface of the second PCB 120, which is oriented opposite the position at which the third PCB 140 is located. Thus, the light emitter/light receiver of the CO2 sensor 40 and the light emitter/light receiver of the dust sensor 60 may have little influence on each other. As a result, it is possible to secure the accuracy of these sensors.

A mount boss 11$f$ may protrude from the bottom 11 of the casing 1. The first PCB 110 may have a first through-hole formed therein to allow the mount boss 11$f$ to pass therethrough. The third PCB 140 may have a second through-hole formed at a position that corresponds to the position of the first through-hole. A screw 92 may pass through the second through-hole from above, and may be fastened into the mount boss 11$f$.

The third PCB 140 may have a first side (e.g. a horizontal side) and a second side (e.g. a vertical side) that intersects the first side. The third PCB 140 may have a substantially rectangular shape. A retaining rib 11$g$ may protrude from the bottom 11. The retaining rib 11$g$ may be formed in an "L" shape that surrounds the first side and the second side to restrain horizontal movement (shaking) of the fourth PCB 130.

The temperature/humidity sensor 70 is mounted on the bottom surface of the first PCB 110. Since the dust sensor 140, the CO2 sensor 40, the VOC sensor 50, and/or the wireless communication interface 80, which are heat-generating elements, are disposed above the first PCB 110, when the temperature/humidity sensor 70 is disposed under the first PCB 110, the heat generated by the above heat-generating elements is blocked and reflected by the first. PCB 110, and does not reach the temperature/humidity sensor 70 hidden under the first. PCB 110. Therefore, the influence of the heat generated by the heat-generating elements on the accuracy of the temperature/humidity sensor 70 is minimized.

Furthermore, when the first PCB 110 is viewed from above, the temperature/humidity sensor 70 may be disposed in a region that does not overlap the CO2 sensor 40. Since the heat generated by the CO2 sensor 40 is not perpendicularly transferred to the first PCB 110, it is possible to reduce an increase in the temperature of the first PCB 110. As a result, the amount of heat transferred to the temperature/humidity sensor 70 from the first PCB 110 through heat conduction may be reduced.

According to the air-quality detection apparatus according to the embodiment of the present disclosure, the temperature/humidity sensor 70 is provided in the casing body 10. Since the temperature/humidity sensor 70 detects the temperature and/or the humidity of air in the casing body 10, the detected value is not completely the same as that of air outside the casing body 10 (e.g. indoor air, hereinafter referred to as "external air"). However, when external air smoothly flows into and out of the casing body 10, the detection value of the temperature/humidity sensor 70 may substantially accurately indicate the state of external air.

In this respect, an air flow passage hole may be formed in the casing in order to allow external air to flow into and out of the space in which the temperature/humidity sensor 70 is accommodated. This air flow passage hole may be used only for ventilation. However, if too many holes are formed in the casing 1, they may mar the aesthetic appearance of the casing 1. Therefore, it is preferable that the air flow passage hole be formed so as to perform not only a ventilation function but also other necessary functions in order to reduce the number of holes.

The air flow passage hole may include at least one vent hole 31, 32 and 33 formed in the cover 30. The dust sensor 60 may include a chamber 61, which is mounted on the top surface of the third PCB 140 and into which air is introduced, and a light emitter (not shown) for emitting light into the chamber 61. The chamber 61 may have at least one communication hole 61$h$1, 61$h$2 and 61$h$3 formed therein to allow external air to flow into and out of the chamber 61.

Air introduced through the at least one vent hole 31, 32 and 33 formed in the cover 30 may be guided to the temperature/humidity sensor 70. A gap g may be formed between the first PCB 110 and the side wall 12. The space between the bottom 11 and the bottom surface of the first PCB 110, which is spaced apart from the bottom 11 by the support rib 11$b$, may communicate with the space above the first PCB 110 through the aforementioned gap.

The at least one vent hole 31, 32 and 33 includes a portion that does not overlap the at least one communication hole 61$h$1, 61$h$2 and 61$h$3. That is, the at least one vent hole 31, 32 and 33 partially communicates with the at least one communication hole 61$h$1, 61$h$2 and 61$h$3 (or overlaps the same when viewed from above). Thus, a portion of external air introduced through the at least one vent hole 31, 32 and 33 enters the chamber 61. However, since there is also a region that does not overlap the at least one vent hole 31, 32 and 33, external air introduced through the non-overlapping region flows from the casing body 10 to the outside of the chamber 61, and reaches the temperature/humidity sensor 70 via the aforementioned gap.

The at least one vent hole 31, 32 and 33 formed in the cover 30 to guide external air to the dust sensor 60 serves as the air flow passage hole through which external air to be guided to the temperature/humidity sensor 70 is introduced.

The air flow passage hole may be a gap formed between the locking hook 23 formed at the exterior panel 20 and hook passages 33$h$1 and 33$h$2 formed in the cover 30. As described above, the locking hook 23 formed at the exterior panel 20 passes through the hook passages 33$h$1 and 33$h$2 formed in the cover 30 and is fitted into the locking recess 15 formed in the casing body 10. In the process of fitting the locking hook 23 into the locking recess 15, a portion of the locking hook 23 that is connected to the lid 21 needs to be elastically deformed. Thus, if the locking hook 23 tightly passes through the hook passages 33*h*1 and 33*h*2, it is difficult to smoothly realize the coupling between the locking hook 23 and the locking recess 15. Therefore, it is preferable that a predetermined gap be present between the locking hook 23 and the hook passages 33*h*1 and 33*h*2. This gap communicates with the interior of the casing body 10.

Air introduced through the gap between the locking hook 23 and the hook passages 33*h*1 and 33*h*2 enters the casino body 10 and reaches the temperature/humidity sensor 70 through the gap between the first. PCB 110 and the side wall 11.

As is apparent from the above description, the air-quality detection apparatus according to the present disclosure has the following effects.

First, when a temperature/humidity sensor and another sensor, which is a heat-generating element, are accommodated in a single casing, the influence of heat generated by the other sensor on the temperature/humidity sensor may be reduced, thereby improving the accuracy of the temperature/humidity sensor. In particular, since interruption of the transfer of heat generated by the other sensor to the temperature/humidity sensor is achieved by the PCB on which the temperature/humidity sensor is mounted, it is not necessary to mount a separate heat insulation material or heat blocking material to interrupt the transfer of heat.

Second, since a flow passage for guiding external air to a temperature/humidity sensor is formed in the casing, it is not necessary to form a separate vent hole in the casing to detect temperature and humidity. As such, since it is not necessary to additionally perforate the casing, the aesthetic design of the casing may be improved.

Third, since PCBs on which sensors are mounted are disposed in a multi-layered structure in a casing, it is possible to conveniently perform assembly and maintenance/repair on the PCBs merely by sequentially stacking or removing the layers.

Fourth, the air quality detected by the sensors may be transmitted over a communication network, and thus a user may conveniently verify the air quality using the user's terminal.

Although the preferred embodiments of the present disclosure have been disclosed for illustrative purposes, those skilled in the art will appreciate that various modifications, additions and substitutions are possible, without departing from the scope and spirit of the disclosure as disclosed in the appended claims.

It will be understood that when an element or layer is referred to as being "on" another element or layer, the element or layer can be directly on another element or layer or intervening elements or layers. In contrast, when an element is referred to as being "directly on" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present invention.

Spatially relative terms, such as "lower", "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over elements described as "lower" relative to other elements or features would then be oriented "upper" relative to the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the disclosure are described herein with reference to cross-section illustrations that are schematic illustrations of idealized embodiments (and intermediate structures) of the disclosure. As such, variations from the shapes of the illustrations as a result, for example, of manufacturing techniques and/or tolerances, are to be expected. Thus, embodiments of the disclosure should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily ail referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An air-quality detection apparatus, comprising:
   a casing body comprising a bottom and a side wall extending upwards from a circumference of the bottom;
   a first printed circuit board (PCB) disposed horizontally above the bottom of the casing body;
   a temperature/humidity sensor mounted on a bottom surface of the first PCB;
   a second PCB disposed horizontally and spaced apart above the first PCB; and
   a $CO_2$ sensor mounted on the second PCB, wherein the $CO_2$ sensor is disposed between the first PCB and the second PCB, wherein a gap is formed between the side wall of the casing body and the first PCB, and wherein a first space formed between the first PCB and the second PCB communicates with a second space formed between the first PCB and the bottom of the casing body through the gap.

2. The air-quality detection apparatus according to claim 1, wherein, when the first PCB is viewed from above, the temperature/humidity sensor is disposed in a region that does not overlap the $CO_2$ sensor.

3. The air-quality detection apparatus according to claim 2, wherein the $CO_2$ sensor is mounted on a bottom surface of the second PCB.

4. The air-quality detection apparatus according to claim 1, wherein the casing body comprises a support rib that protrudes from the bottom thereof to support the bottom surface of the first PCB.

5. The air-quality detection apparatus according to claim 4, wherein the temperature/humidity sensor is disposed within an interval by which the first PCB is spaced apart from the bottom by the support rib.

6. The air-quality detection apparatus according to claim 4, further comprising:
   a third PCB disposed horizontally above the second PCB;
   a dust sensor comprising a chamber mounted on a top surface of the third PCB to receive air introduced thereinto and a light emitter configured to emit light into the chamber, the chamber comprising at least one communication hole formed therein to allow external air to flow into and out of the chamber; and
   a cover configured to cover an open top surface defined opposite the bottom of the casing body by the side wall, the cover comprising at least one vent hole formed therein so as to overlap the at least one communication hole when viewed from above, wherein a portion of the at least one vent hole that does not overlap the at least one communication hole communicates with the gap through a space in the casing body.

7. The air-quality detection apparatus according to claim 6, further comprising:
   an exterior panel comprising a lid disposed above the cover and a locking hook protruding downwards from the lid to be coupled to the casing body, wherein the cover comprises a hook passage formed therein to allow the locking hook to pass therethrough, and wherein a second gap is formed between the locking hook and the hook passage, the second gap communicating with an interior of the casing body.

8. The air-quality detection apparatus according to claim 7, wherein the exterior panel further includes a hinge lock, and the cover includes a hinge lock passage through which the hinge lock passes.

9. The air-quality detection apparatus according to claim 8, wherein the hinge lock and the locking hook are disposed at opposite sides of the lid so as to be symmetrical to each other with respect to a center of the lid.

10. The air-quality detection apparatus according to claim 9, wherein the casing body includes a latching recess and a locking recess configured to mate with the hinge lock and locking hook, respectively.

11. The air-quality detection apparatus according to claim 7, further comprising:
    a pair of stands that protrude from an outer surface of the side wall in a radial direction, wherein the air-quality detection apparatus is configured to stand upright due to the pair of stands such that the exterior panel is oriented in a forward direction.

12. The air-quality detection apparatus according to claim 4, wherein the temperature/humidity sensor is located in the second space.

13. The air-quality detection apparatus according to claim 1, further comprising:
    a third PCB on which a wireless communication interface is mounted, the third PCB being disposed horizontally at a position spaced further upwards apart from the bottom than the first PCB; and
    a processor configured to transmit a detection value of at least one of the $CO_2$ sensor or the temperature/humidity sensor to a communication network through the wireless communication interface.

14. The air-quality detection apparatus according to claim 1, further comprising:
    a volatile organic compound (VOC) sensor mounted a top surface of the first PCB.

15. The air-quality detection apparatus according to claim 14, wherein the VOC sensor includes a heater embedded in a ceramic tube.

16. The air-quality detection apparatus according to claim 14, wherein the VOC sensor is mounted in a second region of the first PCB closer to the sidewall than a first region occupied by the $CO_2$ sensor.

17. The air-quality detection apparatus according to claim 1, further comprising a header pin fan electrically that connects the first PCB to the second PCB.

18. The air-quality detection apparatus according to claim 17, wherein the pin head includes a pin holder located on the bottom surface of the first PCB and a plurality of pin terminals that penetrate the pin holder in a vertical direction.

19. The air-quality detection apparatus according to claim 18, wherein upper portions of the plurality of pin terminals penetrate the second PCB and are connected thereto and lower portions of the plurality of pin terminals penetrate the first PCB and are connected thereto.

20. An air-quality detection apparatus, comprising:
    a casing body comprising a bottom and a side wall extending upwards from a circumference of the bottom;
    a first printed circuit board (PCB) disposed horizontally above the bottom of the casing body;
    a temperature/humidity sensor mounted on a bottom surface of the first PCB;
    a second PCB disposed horizontally above the first PCB;
    a $CO_2$ sensor mounted on the second PCB, wherein the casing body comprises a support rib that protrudes from the bottom thereof to support the bottom surface of the first PCB, wherein a gap is formed between the first, PCB and the side wall such that a space between the bottom and the bottom surface of the first PCB, spaced apart from the bottom by the support rib, communicates with a space above the first PCB therethrough;

a third PCB disposed horizontally above the second PCB;

a dust sensor comprising a chamber mounted on a top surface of the third PCB to receive air introduced thereinto and a light emitter configured to emit light into the chamber, the chamber comprising at least one communication hole formed therein to allow external air to flow into and out of the chamber; and a cover configured to cover an open top surface defined opposite the bottom of the casing body by the side wall, the cover comprising at least one vent hole formed therein so as to overlap the at least one communication hole when viewed from above, wherein a portion of the at least one vent hole that does not overlap the at least one communication hole communicates with the gap through a space in the casing body; and an exterior panel comprising a lid disposed above the cover and a locking hook protruding downwards from the lid to be coupled to the casing body, wherein the cover comprises a hook passage formed therein to allow the locking hook to pass therethrough, and wherein a second gap is formed between the locking hook and the hook passage, the second gap communicating with an interior of the casing body.

\* \* \* \* \*

UNITED STATES PATENT AND TRADEMARK OFFICE
CERTIFICATE OF CORRECTION

PATENT NO.         : 11,516,918 B2
APPLICATION NO.    : 16/705695
DATED              : November 29, 2022
INVENTOR(S)        : Chiwan Park et al.

Page 1 of 1

It is certified that error appears in the above-identified patent and that said Letters Patent is hereby corrected as shown below:

On the Title Page

Item [30], insert:
--December 7, 2018 (KR).................................................... 10-2018-0157580--

Signed and Sealed this
Third Day of January, 2023

Katherine Kelly Vidal
*Director of the United States Patent and Trademark Office*